(12) United States Patent
Pitcovski et al.

(10) Patent No.: US 8,168,750 B2
(45) Date of Patent: May 1, 2012

(54) SUBUNITS OF THE ADENOVIRUS FIBER PROTEIN AND USES THEREOF AS VACCINES

(75) Inventors: Jacob Pitcovski, Korazim (IL); Elena Fingerut, Carmiel (IL); Bezalel Gutter, Jerusalem (IL); Gilad Gallili, Jerusalem (IL); Amnon Michael, Hofit (IL)

(73) Assignee: ABIC Biological Laboratories Ltd., Beit Shemesh (IL)

( * ) Notice: Subject to any disclaimer, the term of this patent is extended or adjusted under 35 U.S.C. 154(b) by 0 days.

(21) Appl. No.: 12/960,932

(22) Filed: Dec. 6, 2010

(65) Prior Publication Data

US 2011/0159024 A1    Jun. 30, 2011

Related U.S. Application Data

(62) Division of application No. 10/547,878, filed as application No. PCT/IL03/00169 on Mar. 4, 2003, now Pat. No. 7,858,766.

(51) Int. Cl.
*C07K 14/00* (2006.01)
*A61P 31/20* (2006.01)
*A61K 39/235* (2006.01)

(52) U.S. Cl. ..... 530/350; 514/3.7; 424/186.1; 424/233.1

(58) Field of Classification Search ................ None
See application file for complete search history.

(56) References Cited

U.S. PATENT DOCUMENTS 7,858,766 B2 * 12/2010 Pitcovski et al. .......... 536/23.72
2007/0053935 A1    3/2007 Pitcovski et al.

FOREIGN PATENT DOCUMENTS

| EP | 0 952 214 A1 | 10/1999 |
| WO | WO 97/40180 | 10/1997 |
| WO | WO 99/31249 | 6/1999 |

OTHER PUBLICATIONS

PCT International Preliminary Report on Patentability issued on Sep. 4, 2005 in connection with PCT/IL03/00169, filed on Mar. 4, 2003.
PCT International Search Report issued by the International Searching Authority on Mar. 8, 2004 in connection with related International Application No. PCT/IS2003/000169.
Database EMBL online, Feb. 21, 1997, Akopian T et al: "Eggdrop syndrome-1976 virus fiber gene" retrieved from EBI, database accession No. Z86065.
Doonan, S. (1998) "Protein Purification Protocol," 59:31-37.
Edbauer, C. et al. (1990) "Protection of Chickens with a Recombinant Fowlpox Virus Expressing the Newcastle Disease Virus Hemagglutinin-Neuraminidase Gene" Virology 179:901.
Fadly, A.M. et al. (1989) "Hemorrhagic Enteritis of Turkeys: Influence of Maternal Antibody and Age at Exposure" Avian Diseases 33:778-786.
Fingerut, E. et al. (2001) Development of a subunit vaccine to EDS. In XXXVIII Ann. Conv. World Poultry Sci. Assoc. (original Hebrew document and English translation).
Fingerut, E. et al. (2003) "A Subunit Vaccine Against the Adenovirus Egg-Drop Syndrome Using Part of Its Fiber Protein" Vaccine 2761-2766.
Harris, J.R. et al. (1976) "Hemorrhagic Enteritis in Two-and-One-Half-Week-Old Turkey Poults" Avian Diseases 21(1):120-122.
Henry, L. J., et al. (1994). Characterization of the Knob Domain of the Adenovirus Type 5 Fiber Protein Expressed in *Escherichia coli*. J. Virol. 68: 5239-5246.
Jucker, M.T. et al. (1996) "Characterization of the Haemorrhagic Enteritis Virus Genome and the Sequence . . . " J. of General Virology 77:469-479.
Laemmli, U.K. (1970) "Cleavage of Structural Proteins During the Assembly of the Head of Bacteriophage T4" Nature 227:680-685.
Nazerian, K. et al. (1991) "Structural Polypeptides of Type II Avian Adenoviruses Analyzed by Monoclonal and Polyclonal Antibodies" Avian Diseases 35:572-578.
Owaga, R. et al. (1990) "Recombinant Fowlpox Viruses Inducing Protective Immunity Against Newcastle Disease and Fowlpox Viruses" Vaccine 8:486-490.
Pitcovski, J. et al. (1998) "The Complete DNA Sequence and Genome Organization of the Avian Adenovirus, Hemorrhagic Enteritis Virus" Virology 249:307-315.
Pitcovski, J. et al. (1996) "Insect Cell-derived VP2 of Infectious Bursal Disease Virus Confers Protection Against the Disease in Chickens" Avian Diseases 40:753-761.
Pitcovski, J. et al. (2005) "A subunit vaccine strategy against hemorrhagic enteritis adenovirus", Vaccine, vol. 23: 4697-4702.
Schnitzlein, W.M. et al. (1988) "Genomic and Antigenic Characterization of Avipoxviruses" Virus Research 10:65-76.
Solyom, E. et al. (1982) "Studies on Eds Vaccine" Develop. Biol. Standard 51:105-121.
Taylor, J. et al. (1988) "Protective Immunity Against Avian Influenza Induced by a Fowlpox Virus Recombinant" Vaccine 6:504-508.
Tripathy, D.N. et al. (1990) "Regulation of Foreign Gene in Fowlpox Virus by a Vaccine Virus Promoter" Avian Diseases 34:218-220.
van den Hurk, J. V., et al. (1986) "Quantitation of Hemorrhagic Enteritis Virus Antigen and Antibody using Enzyme-Linked Immunosorbent Assays" Avian Diseases 30(4):662-671.
van den Hurk, J.V., et al. (1993) "Protection of Turkeys Against Haemorrhagic Enteritis by Monoclonal Antibody and hexon Immunization" Vaccine 11(3):329-335.
Yuying, T. et al. (2004) "Poster Category: Transgenics and Biotechnology" XP-002267947 (Abstract only).

(Continued)

*Primary Examiner* — Michael Burkhart
(74) *Attorney, Agent, or Firm* — John P. White; Cooper & Dunham LLP

(57) ABSTRACT

A nucleic acid sequence encoding a fragment of the adenovirus fiber capsid protein, a DNA construct including a replicable expression vector and at least one heterologous nucleic acid, and recombinant protein including fragment of the adenovirus fiber capsid protein. The fragment comprises the C-terminal knob and part of the shaft domain of the fiber protein of these adenoviruses. The use of recombinant proteins as an active ingredient in vaccinating compositions for conferring to an animal immunity against a pathogenic infection by an adenovirus, and methods for vaccinating a domestic bird against a pathogenic adenoviral infection.

10 Claims, 4 Drawing Sheets

OTHER PUBLICATIONS

Aug. 27, 2007 Office Action issued by the U.S. Patent and Trademark Office in connection with U.S. Appl. No. 10/547,878.

Oct. 11, 2007 Response filed in Response to Aug. 27, 2007 Office Action issued by the U.S. Patent and Trademark Office in connection with U.S. Appl. No. 10/547,878.

Jan. 30, 2008 Office Action issued by the U.S. Patent and Trademark Office in connection with U.S. Appl. No. 10/547,878.

May 30, 2008 Response filed in Response to Jan. 30, 2008 Office Action issued by the U.S. Patent and Trademark Office in connection with U.S. Appl. No. 10/547,878.

Sep. 19, 2008 Office Action issued by the U.S. Patent and Trademark Office in connection with U.S. Appl. No. 10/547,878.

Nov. 14, 2008 Comm. filed in Response to Sep.19, 2008 Office Action issued by the U.S. Patent and Trademark Office in connec. with U.S. Appl. No. 10/547,878.

Mar. 17, 2009 Comm. filed in Rsp to Feb. 17, 2009 Notice of Non-Compliant Amendment issued by the U.S. Patent and Trademark Office in conn. with U.S. Appl. No. 10/547,878.

Jun. 5, 2009 Final Office Action issued by the U.S. Patent and Trademark Office in connection with U.S. Appl. No. 10/547,878.

Nov. 5, 2009 Amendment filed in Response to Jun. 5, 2009 Final Office Action issued by the U.S. Patent and Trademark Office in connection with U.S. Appl. No. 10/547,878.

Dec. 28, 2009 Office Action issued by the U.S. Patent and Trademark Office in connection with U.S. Appl. No. 10/547,878.

Mar. 25, 2010 Amendment filed in Response to Dec. 28, 2009 Office Action issued by the U.S. Patent and Trademark Office in connection with U.S. Appl. No. 10/547,878.

Apr. 29, 2010 Final Office Action issued by the U.S. Patent and Trademark Office in connection with U.S. Appl. No. 10/547,878.

Jul. 20, 2010 Amend. Under 37 C.F.R. §1.116In Rsp to Apr. 29, 2010 Final Office Action issued by the U.S. Patent and Trademark Office in conn. with U.S. Appl. No. 10/547,878.

Aug. 19, 2010 Notice of Allowability issued by the U.S. Patent and Trademark Office in connection with U.S. Appl. No. 10/547,878.

* cited by examiner

```
MATPGKRSAE    EPDQQTLKKS                          | N' term
KQSDQSQGLN    LAYPFDKITE
FEATPPFIHV    GQGLDISD LSL     NMRIG     KGL    KFENGNLVVS
DQQ     YNVTP     PLI    ADQST
LGL     KYNP      DVL    SLTH
SGA     LTLP      TIQ    HPLQASAGK
FEL     ALSSG     LKS    DDQG
LTL     DLDP      VFS    TESSK               Shaft
FLL     NCSLP     LDK    NSDK
LTL     KFGNG     LGL    NNDQLE
NTM     TYNLP     LKR    DG
TNV     SLSFG     TNF    KILNEM
LTL     NLVAP     MSN    SAGG
LAL     QFKSP     LSA    DDGI
LSI     KTPTSLG   ITG    NKLG
IRL     APNSG     LQI    TPNGLAVSVN
AVQ     ILSSP     LIT    AASI
GPP     TTNVTG    TVS PGRATNGQFV    TKTAKVLRYK
FVRWDALLII    QFIDNIGVIE
NPTFYRNKSI    ELRSADFLSP
TLNNTYIVPL    NGGVRVESPT               Knob
IPVQLEVILE    NNSSFIQVGF
VRLTVKNGNP    HMIIQCNPVP
GNIKMIKIKS    VMLFTCLIG
```

Fig. 1

Shaft: N-  LTL AYDST DFQ VTENG
            LAL KVSPT QTP LTRIISM

Knob: 443 - GNNLFDSGYEIFASCPQNKAAKVAGYVVYLTSVGSLVHGTIQIK
          ATAGYWFTGGNSVQESIRFGLVLCPFSARDPTANLSGWPAPVVWSGDSN
          TPLYFAANAISYTNNRVNLAVTGNFYKEETELPGYTRHSFCPTGTTGMN
          FTGGNLYVCPCTVNTGATTLNAIYMVFVITQSALGTNFFASNTPPNTFF
          LTPPIPFTYVGAQ              -644

SEQUENCE LISTING

```
<160> NUMBER OF SEQ ID NOS: 15

<210> SEQ ID NO 1
<211> LENGTH: 564
<212> TYPE: DNA
<213> ORGANISM: HEV virus

<400> SEQUENCE: 1
ataagattgg cccctaacag tggtctgcaa ataacaccaa atggtctagc agttagtgtt     60
aatgctgtgc aaattctaag tagtccttta attactgcag cgtctatagg cccaccaaca    120
acaatggtta ctggaacagt gtcaccgggc agagcaacaa atggtcaatt tgtaaccaaa    180
actgctaaag ttttacgtta taaatttgtg agatgggatg ctctgttaat catacagttt    240
atagataaca taggtgtaat agaaaaccct acctttatc gtaacaaaag tattgaatta    300
agatctgctg atttcttgag tcctacgtta aataatacat atatagtgcc attgaatgga    360
ggggtaaggg tagaatcacc tactattcct gtacaattag aagttatact tgaaaacaat    420
tcctctttca ttcaagtagg gtttgttagg ttaacagtta agaatggtaa ccctcatatg    480
attattcagt gtaatcctgt acctgggaat attaaaatga taaagataaa atctgtaatg    540 cttttttactt gtttgatagg ctga                                          564

<210> SEQ ID NO 2
<211> LENGTH: 714
<212> TYPE: DNA
<213> ORGANISM: EDS virus

<400> SEQUENCE: 2
ttgactttgg cttatgattc cacggatttt caggtgacag aaaacggtct ggccctaaag     60
gtatctccga cgcagacccc tctcaccaga ataatttcta tgggaaataa cttgtttgat    120
tctggttatg agatttttgc ttcatgtccg cagaacaaag cagcaaaggt tgcagggtat    180
gtgtatttaa catcggttgg tgggcttgta catgggacca ttcagattaa agctactgcg    240
gggtattggt ttacggggggg aaacagcgtg caggaaagta tcaggtttgg attggtgttg    300
```

```
tgtccttta gtgctcgcga ccccactgct aacctgtcag gctggccagc gccagtagtg    360
tggagtggtg atagcaatac tccctatat tttgcggcca atgccattag ttataccaat    420
aaccgtgtaa atcttgcagt taccggtaac ttttacaagg aggaaaccga attgccgggt    480
tacactcgtc attctttctg ccctaccggg accaccggaa tgaattttac aggggtaat    540 ttgtatgtgt gtccgtgcac tgtaaataca ggggccacca cactgaatgc catttatatg    600
gtgtttgtga ttactcaatc agctttggga actaatttct ttgcttctaa caccccctccc    660 aacacattct ttttaactcc ccccattccc tttacatatg ttggagcaca gtag          714
```

<210> SEQ ID NO 3
<211> LENGTH: 187
<212> TYPE: PRT
<213> ORGANISM: HEV virus

<400> SEQUENCE: 3

```
Ile Arg Leu Ala Pro Asn Ser Gly Leu Gln Ile Thr Pro Asn Gly Leu
1               5                   10                  15

Ala Val Ser Val Asn Ala Val Gln Ile Leu Ser Ser Pro Leu Ile Thr
            20                  25                  30

Ala Ala Ser Ile Gly Pro Pro Thr Thr Asn Val Thr Gly Thr Val Ser
        35                  40                  45

Pro Gly Arg Ala Thr Asn Gly Gln Phe Val Thr Lys Thr Ala Lys Val
    50                  55                  60

Leu Arg Tyr Lys Phe Val Arg Trp Asp Ala Leu Leu Ile Ile Gln Phe
65                  70                  75                  80

Ile Asp Asn Ile Gly Val Ile Glu Asn Pro Thr Phe Tyr Arg Asn Lys
                85                  90                  95

Ser Ile Glu Leu Arg Ser Ala Asp Phe Leu Ser Pro Thr Leu Asn Asn
            100                 105                 110

Thr Tyr Ile Val Pro Leu Asn Gly Gly Val Arg Val Glu Ser Pro Thr
        115                 120                 125

Ile Pro Val Gln Leu Glu Val Ile Leu Glu Asn Asn Ser Ser Phe Ile
    130                 135                 140

Gln Val Gly Phe Val Arg Leu Thr Val Lys Asn Gly Asn Pro His Met
145                 150                 155                 160

Ile Ile Gln Cys Asn Pro Val Pro Gly Asn Ile Lys Met Ile Lys Ile
                165                 170                 175

Lys Ser Val Met Leu Phe Thr Cys Leu Ile Gly
            180                 185
```

<210> SEQ ID NO 4
<211> LENGTH: 237
<212> TYPE: PRT
<213> ORGANISM: EDS virus

<400> SEQUENCE: 4

```
Leu Thr Leu Ala Tyr Asp Ser Thr Asp Phe Gln Val Thr Glu Asn Gly
1               5                   10                  15

Leu Ala Leu Lys Val Ser Pro Thr Gln Thr Pro Leu Thr Arg Ile Ile
            20                  25                  30

Ser Met Gly Asn Asn Leu Phe Asp Ser Gly Tyr Glu Ile Phe Ala Ser
        35                  40                  45

Cys Pro Gln Asn Lys Ala Ala Lys Val Ala Gly Tyr Val Tyr Leu Thr
    50                  55                  60

Ser Val Gly Ser Leu Val His Gly Thr Ile Gln Ile Lys Ala Thr Ala
```

```
                65                  70                  75                  80
Gly Tyr Trp Phe Thr Gly Gly Asn Ser Val Gln Glu Ser Ile Arg Phe
                        85                  90                  95

Gly Leu Val Leu Cys Pro Phe Ser Ala Arg Asp Pro Thr Ala Asn Leu
                100                 105                 110

Ser Gly Trp Pro Ala Pro Val Val Trp Ser Gly Asp Ser Asn Thr Pro
                115                 120                 125

Leu Tyr Phe Ala Ala Asn Ala Ile Ser Tyr Thr Asn Asn Arg Val Asn
            130                 135                 140

Leu Ala Val Thr Gly Asn Phe Tyr Lys Glu Glu Thr Glu Leu Pro Gly
145                 150                 155                 160

Tyr Thr Arg His Ser Phe Cys Pro Thr Gly Thr Thr Gly Met Asn Phe
                    165                 170                 175

Thr Gly Gly Asn Leu Tyr Val Cys Pro Cys Thr Val Asn Thr Gly Ala
                180                 185                 190

Thr Thr Leu Asn Ala Ile Tyr Met Val Phe Val Ile Thr Gln Ser Ala
                195                 200                 205

Leu Gly Thr Asn Phe Phe Ala Ser Asn Thr Pro Asn Thr Phe Phe
            210                 215                 220

Leu Thr Pro Pro Ile Pro Phe Thr Tyr Val Gly Ala Gln
225                 230                 235

<210> SEQ ID NO 5
<211> LENGTH: 33
<212> TYPE: DNA
<213> ORGANISM: Artificial Sequence
<220> FEATURE:
<223> OTHER INFORMATION: 5' primer for H-knob-s construct

<400> SEQUENCE: 5
cggggtacca ataagattgg cccctaacag tgg                                    33

<210> SEQ ID NO 6
<211> LENGTH: 34
<212> TYPE: DNA
<213> ORGANISM: Artificial Sequence
<220> FEATURE:
<223> OTHER INFORMATION: 3' primer for the H-knob-s construct

<400> SEQUENCE: 6
cgctctagat cagcctatca aacaagtaaa aagc                                   34

<210> SEQ ID NO 7
<211> LENGTH: 31
<212> TYPE: DNA
<213> ORGANISM: Artificial Sequence
<220> FEATURE:
<223> OTHER INFORMATION: 5' primer for the E-knob-s construct

<400> SEQUENCE: 7
gcgggtacct ttgactttgg cttatgattc c                                      31

<210> SEQ ID NO 8
<211> LENGTH: 29
<212> TYPE: DNA
<213> ORGANISM: Artificial Sequence
<220> FEATURE:
<223> OTHER INFORMATION: 3' primer for the E-knob-s-construct

<400> SEQUENCE: 8
atatctagac tactgtgctc caacatatg                                         29
```

```
<210> SEQ ID NO 9
<211> LENGTH: 49
<212> TYPE: DNA
<213> ORGANISM: Artificial Sequence
<220> FEATURE:
<223> OTHER INFORMATION: 5' primer of Fiber construct

<400> SEQUENCE: 9
gcgggtacct atgctacacc atcaccatca caagcgacta cggttggac           49

<210> SEQ ID NO 10
<211> LENGTH: 29
<212> TYPE: DNA
<213> ORGANISM: Artificial Sequence
<220> FEATURE:
<223> OTHER INFORMATION: 3' primer of Fiber construct

<400> SEQUENCE: 10
atatctagac tactgtgctc caacatatg                                 29

<210> SEQ ID NO 11
<211> LENGTH: 26
<212> TYPE: DNA
<213> ORGANISM: Artificial Sequence
<220> FEATURE:
<223> OTHER INFORMATION: 5' primer of the Hexon construct

<400> SEQUENCE: 11
cggggtacct atggaacccc aacgtg                                    26

<210> SEQ ID NO 12
<211> LENGTH: 26
<212> TYPE: DNA
<213> ORGANISM: Artificial Sequence
<220> FEATURE:
<223> OTHER INFORMATION: 3' primer of the Hexon construct

<400> SEQUENCE: 12
gctctagatc atgttgctgc actacc                                    26

<210> SEQ ID NO 13
<211> LENGTH: 453
<212> TYPE: PRT
<213> ORGANISM: HEV Fiber Protein

<400> SEQUENCE: 13

Met Ala Thr Pro Gly Lys Arg Ser Ala Glu Glu Pro Asp Gln Gln Thr
 1               5                  10                  15

Leu Lys Lys Ser Lys Gln Ser Asp Gln Ser Gly Leu Asn Leu Ala Tyr
            20                  25                  30

Pro Glu Asp Lys Ile Thr Glu Phe Glu Ala Thr Pro Pro Phe Ile His
        35                  40                  45

Val Gly Gln Gly Leu Asp Ile Ser Asp Leu Ser Leu Asn Met Arg Ile
    50                  55                  60

Gly Lys Gly Leu Lys Glu Glu Asn Gly Asn Leu Val Val Ser Asp Gln
65                  70                  75                  80

Gln Tyr Asn Val Thr Pro Pro Leu Ile Ala Asp Gln Ser Thr Leu Gly
                85                  90                  95

Leu Lys Tyr Asn Pro Asp Val Leu Ser Leu Thr His Ser Gly Ala Leu
            100                 105                 110

Thr Leu Pro Thr Ile Gln His Pro Leu Gln Ala Ser Ala Gly Lys Phe
        115                 120                 125
```

```
Glu Leu Ala Leu Ser Ser Gly Leu Lys Ser Asp Asp Gln Gly Leu Thr
            130                 135                 140

Leu Asp Leu Asp Pro Val Phe Ser Thr Glu Ser Ser Lys Phe Leu Leu
145                 150                 155                 160

Asn Cys Ser Leu Pro Leu Asp Lys Asn Ser Asp Lys Leu Thr Leu Lys
                165                 170                 175

Phe Gly Asn Gly Leu Gly Leu Asn Asn Asp Gln Leu Glu Asn Thr Met
            180                 185                 190

Thr Tyr Asn Leu Pro Leu Lys Arg Asp Gly Thr Asn Val Ser Leu Ser
                195                 200                 205

Phe Gly Thr Asn Phe Lys Ile Leu Asn Glu Met Leu Thr Leu Asn Leu
            210                 215                 220

Val Ala Pro Met Ser Asn Ser Ala Gly Gly Leu Ala Leu Gln Phe Lys
225                 230                 235                 240

Ser Pro Leu Ser Ala Asp Asp Gly Ile Leu Ser Ile Lys Thr Pro Thr
                245                 250                 255

Ser Leu Gly Ile Thr Gly Asn Lys Leu Gly Ile Arg Leu Ala Pro Asn
            260                 265                 270

Ser Gly Leu Gln Ile Thr Pro Asn Gly Leu Ala Val Ser Val Asn Ala
            275                 280                 285

Val Gln Ile Leu Ser Ser Pro Leu Ile Thr Ala Ala Ser Ile Gly Pro
290                 295                 300

Pro Thr Thr Asn Val Thr Gly Thr Val Ser Pro Gly Arg Ala Thr Asn
305                 310                 315                 320

Gly Gln Phe Val Thr Lys Thr Ala Lys Val Leu Arg Tyr Lys Phe Val
            325                 330                 335

Arg Trp Asp Ala Leu Leu Ile Ile Gln Phe Ile Asp Asn Ile Gly Val
            340                 345                 350

Ile Glu Asn Pro Thr Phe Tyr Arg Asn Lys Ser Ile Glu Leu Arg Ser
            355                 360                 365

Ala Asp Phe Leu Ser Pro Thr Leu Asn Asn Thr Tyr Ile Val Pro Leu
            370                 375                 380

Asn Gly Gly Val Arg Val Glu Ser Pro Thr Ile Pro Val Gln Leu Glu
385                 390                 395                 400

Val Ile Leu Glu Asn Asn Ser Ser Phe Ile Gln Val Gly Phe Val Arg
                405                 410                 415

Leu Thr Val Lys Asn Gly Asn Pro His Met Ile Ile Gln Cys Asn Pro
                420                 425                 430

Val Pro Gly Asn Ile Lys Met Ile Lys Ile Lys Ser Val Met Leu Phe
            435                 440                 445

Thr Cys Leu Ile Gly
    450

<210> SEQ ID NO 14
<211> LENGTH: 34
<212> TYPE: PRT
<213> ORGANISM: EDS Fiber Protein

<400> SEQUENCE: 14

Leu Thr Leu Ala Tyr Asp Ser Thr Asp Phe Gln Val Thr Glu Asn Gly
1               5                   10                  15

Leu Ala Leu Lys Val Ser Pro Thr Gln Thr Pro Leu Thr Arg Ile Ile
                20                  25                  30

Ser Met
```

-continued

```
<210> SEQ ID NO 15
<211> LENGTH: 203
<212> TYPE: PRT
<213> ORGANISM: EDS Fiber Protein

<400> SEQUENCE: 15

Gly Asn Asn Leu Phe Asp Ser Gly Tyr Glu Ile Phe Ala Ser Cys Pro
1               5                   10                  15

Gln Asn Lys Ala Ala Lys Val Ala Gly Tyr Val Tyr Leu Thr Ser Val
            20                  25                  30

Gly Ser Leu Val His Gly Thr Ile Gln Ile Lys Ala Thr Ala Gly Tyr
        35                  40                  45

Trp Phe Thr Gly Gly Asn Ser Val Gln Glu Ser Ile Arg Phe Gly Leu
    50                  55                  60

Val Leu Cys Pro Phe Ser Ala Arg Asp Pro Thr Ala Asn Leu Ser Gly
65                  70                  75                  80

Trp Pro Ala Pro Val Val Trp Ser Gly Asp Ser Asn Thr Pro Leu Tyr
                85                  90                  95

Phe Ala Ala Asn Ala Ile Ser Tyr Thr Asn Asn Arg Val Asn Leu Ala
            100                 105                 110

Val Thr Gly Asn Phe Tyr Lys Glu Glu Thr Glu Leu Pro Gly Tyr Thr
        115                 120                 125

Arg His Ser Phe Cys Pro Thr Gly Thr Thr Gly Met Asn Phe Thr Gly
    130                 135                 140

Gly Asn Leu Tyr Val Cys Pro Cys Thr Val Asn Thr Gly Ala Thr Thr
145                 150                 155                 160

Leu Asn Ala Ile Tyr Met Val Phe Val Ile Thr Gln Ser Ala Leu Gly
                165                 170                 175

Thr Asn Phe Phe Ala Ser Asn Thr Pro Pro Asn Thr Phe Phe Leu Thr
            180                 185                 190

Pro Pro Ile Pro Phe Thr Tyr Val Gly Ala Gln
        195                 200
```

SUBUNITS OF THE ADENOVIRUS FIBER PROTEIN AND USES THEREOF AS VACCINES

This application is a divisional of U.S. Ser. No. 10/547,878 now U.S. Pat. No. 7,858,766, which is a §371 National Stage of PCT International Application No. PCT/IL2003/000169, filed Mar. 4, 2003, the contents of each of which are hereby incorporated by reference in their entirety.

FIELD OF THE INVENTION

The present invention relates to a nucleic acid sequence encoding a fragment of the adenovirus fiber capsid protein, which fragment comprises the C-terminal knob domain and part of the shaft domain. The invention further relates to DNA constructs comprising said DNA fragment, to recombinant proteins encoded thereby, and more particularly, their use as vaccinating compositions against adenovirus pathogenic infections.

BACKGROUND OF THE INVENTION

One of the most important economic goals in the poultry industry is to minimize losses caused by infectious diseases by means of effective vaccines. Among the prominent virus pests are avian adenoviruses which cause various diseases in poultry. Adenoviruses are double-stranded DNA viruses with a genome in the range of 25-45 kb [Jucker et al., J. General. Virol. 77:469-479 (1996)]. The virus consists of 11 proteins with molecular weights ranging from 14 kD to 97 kD [Nazerian, K, et al., Avian Dis. 35:572-578 (1991)]. The polypeptide 97 kD, hexon, is a monomer of the major outer capsid. Other capsid proteins include the structural protein penton, and fiber proteins which are involved in the interaction with cell receptors during virus penetration into the cell.

One of the main diseases in turkeys is caused by the avian adenovirus Hemorrhagic Enteritis virus (HEV). The virus suppresses elements of the immune system by destroying B cells and macrophages. As a result, the immune response to diseases is decreased, as well as the effectiveness of response to various vaccines. The disease is especially prevalent during the ages 7-9 weeks [Domermuth, C. H. and Gross, W. B., 1984, Diseases of poultry, Iowa State University press, Ames, Iowa, 8th Edition (1984) pp. 511-516] when the birds are no longer protected by maternal antibodies [Van den Hurk, J. V., Avian Dis. 30:662-671 (1986); Harris, J. R., and Domermuth, C. H., Avian Dis. 21:120-122 (1977); Fadly, A. M., and Nazerian K, Avian Dis., 33:778.786 (1989)]. Heavy financial losses result from outbreaks of HEV, with its symptoms of weight loss and mortality. Furthermore, outbreaks of other diseases can follow as result of lowered resistance.

Another poultry disease caused by an adenovirus, is the egg drop syndrome. The virus was detected in 1976 [Van Eck, J. H. H. F. G. Davelaar, T. A. M., Avian Pathol., 5:261-272 (1976)], and is designated as strain 127 [McCracken, R. M. and McFerran, J. B., Avian Pathol, 7:483-490 (1978)]. The Egg prop Syndrome virus leads to creation of eggs having a thinner shell or to shell-less eggs. These phenomena cause a significant reduction in egg production throughout the world and therefore lead to economic losses [McFerran, J. B., Rowley, H. M., McNulty, M. S., and Montgomery, L. J., Avian Pathol., 6:405-413 (1997)]. The virus is transmitted through direct or indirect contact with infected fowl. The main way the virus spreads is by vertical transmission, from hen to eggs, which can be prevented only by keeping uninfected flocks as a source for further breeding. There is no successful treatment of the disease.

A conventional vaccination against HEV is made either by inactivated virus, or by a live vaccine of low virulence, for example by an attenuated virus [Fadly and Nazerian (1989)]. The live vaccines may show a disadvantage of antigenic coverage not identical to the virulent strain. On the other hand, the commercially available inactivated vaccines may expose the animals to an unnecessary wide range of antigens. Another vaccination against EDS has been also described [Baxendale, W., Lutticken, D., Hein, R., and McPherson, I., Avia Pathol., 9:77-91 (1980); Solyom, F., Nemesi, M., Forgacs, A., Balla, E., and Perenyi, T., Dev. Biol. Stand., 51:105-121 (1982)]. It is performed at the age 14-16 weeks by inactivated vaccine in oil adjuvant, and it confers one-year protection against clinical symptoms. The use of attenuated vaccines, and even inactivated ones, always bears a danger due to the possibility that the inactivation may be incomplete, or that the mild, attenuated virus will revert to virulence.

It is therefore an object of this invention to provide a safe vaccine against HEV and against EDS that eliminates the danger of an outbreak of the disease which is inherent to the use of live or inactivated vaccines, as a result of reversion of the virus to virulence, or its incomplete inactivation. It is a further object of this invention to protect poultry against a wide antigenic range of the virulent field viruses. Another purpose of this invention is to prevent unnecessary exposure of the birds to non-relevant antigens during the vaccination.

There is an additional problem in a conventional vaccination against HEV; the heavy expenditure involved in relying on spleen tissue from live turkeys for propagation of the virus in large quantities. The inactivated vaccines used at present against HEV are expensive and involve mass infection of birds in order to isolate the virus from the spleen.

Recombinant technology enabled construction of new vaccines. Efficacy of immunization by the recombinant virus has been reported for a number of disease-causing viruses. The infection of birds by the recombinant virus, that expresses the protein hemaglutinin of Avian Influenza, provided protection to birds exposed to this disease [Taylor. J., et al., Vaccine 6:504-508 (1988); Tripathy, D. N., and Wittek. R., Avian Dis. 34:218-220 (1990)]. The immunization of birds with recombinant FPV, into which the gene of the HN protein of the Newcastle Disease Virus (NDV) had been inserted, induced production of antibodies which protected them against the disease (Edbauer C., et Virology, 179:901-904 (1990)]. Furthermore, it was found that the birds which had been immunized with this recombinant virus developed resistance to NDV without any decrease in the resistance to FPV [Ogawa, R., at al., Vaccine 8: 486-490 (1990)]. Recombinants of this sort are effective for the delivery of vaccines to birds [Schnitzlein W. M., et al., Virus Res. 10: 65-76 (1988)]. Evidently, protecting against two diseases by one vaccine makes vaccination considerably cheaper.

In developing a poultry vaccine, a number of factors concerning the poultry industry must be taken into account. Since the price of a single bird is relatively very low, one of the most important factors is the cost of the vaccine. A vaccination by a subunit viral protein might be an inexpensive approach. This approach would also eliminate the said danger of reversion to virulence, since a subunit vaccine cannot replicate. Another advantage would be elimination of unnecessary exposure to a variety of antigens. The effectiveness of subunit viral vaccines has been tested in the inventors' laboratory on Infectious Bursal Disease virus, whose VP2 was expressed in baculovirus expression system, and it conferred full protection against the disease [Pitcovski. J., et al., Avian Dis. 40:753-761 (1996)]. Other subunit vaccines have been found efficient, including vaccine against hepatitis B in humans.

Subunit vaccine against EDS virus based on the fiber protein, have been previously reported by the inventors Fingerut, E., B. Gutter, G. Gallili, A. Michael, and J. Pitcovski. 2001. Development of a subunit vaccine to EDS.

In: xxXVIII Ann. Conv. World Poultry Sci. Assoc. (Hebrew).

In this publication, the present inventors describe creation of recombinant EDS fiber protein and use thereof as vaccine against EDS. However, as shown by the following Examples, and particularly in Example 5, the vaccine of the present invention which is based on a specific fragment of the fiber protein, is significantly more efficient as an anti-EDS vaccine 33% vs. 100% virus neutralization). The Fiber fragment used in the present invention comprises the knob domain and part of the N' terminal shaft domain of the fiber protein. Interestingly, use of the corresponding fragment in another avian adenovirus, HEV as exemplified in the present invention (Examples 1 to 3), efficiently protects treated birds against HEV. Therefore, the particular use of certain fragments of the fiber protein in the recombinant protein of the invention leads to development of an efficient anti-adenbvirus vaccine.

It is therefore an object of the present invention to provide subunit vaccines against adenoviruses. Such vaccinating compositions comprise as an active ingredient recombinant protein comprising a fragment of the fiber protein of any adenovirus. This specific recombinant protein is capable of eliciting a protective immunity in any infected animal, against said adenoviral pathogen. More specifically, the recombinant protein of the invention is intended for vaccinating human or any domestic animal against adenoviral infection. For example, particular object of this invention is to protect poultry against two economically main diseases, HEV and EDS, by producing immunogenic proteins of both EDS virus and HE virus as subunit vaccines.

SUMMARY OF THE INVENTION

In a first aspect the present invention relates to a nucleic acid sequence encoding a fragment of the adenovirus fiber capsid protein which is capable of binding to the target cell. The fragment according to the present invention comprises the C-terminal knob domain and at least 10 to 100 amino acids of the shaft domain of the adenovirus fiber protein, which is immediately N' terminal adjacent to said knob domain. Preferably, the nucleic acid sequence of the invention encodes a fragment comprising the C-terminal knob domain and at least 20 to 60 amino acids of the shaft domain of said adenovirus fiber protein.

According to another specific embodiment, the nucleic acid sequence according to the invention encodes a fragment of the fiber protein of any one of HEV (Hemorrhagic enteritis virus) or EDS (Egg drop syndrome virus).

A specifically preferred embodiment relates to the nucleic acid sequence according to the invention, wherein said adenovirus is HEV (Hemorrhagic enteritis virus). In this embodiment, the fragment encoded by the nucleic acid sequence of the invention comprises the C-terminal knob domain and the adjacent 48 amino acids of the shaft domain of the HEY fiber capsid protein. Preferably, in this embodiment the nucleic acid sequence is substantially as denoted by SEQ ID NO: 1 or functional homologues and fragments thereof.

In another specifically preferred embodiment, the adenovirus is EDS (Egg drop syndrome virus). In this embodiment, the fragment encoded by the nucleic acid sequence of the invention comprises the C-terminal knob domain and the adjacent 34 amino acids of the shaft domain of the EDS fiber capsid protein. Preferably, in this embodiment the nucleic acid sequence is substantially as denoted by SEQ ID NO: 2 or functional homologues and fragments thereof.

In a second aspect, the present invention relates to a DNA construct comprising a replicable expression vector and at least one heterologous nucleic acid sequence encoding a fragment of the adenovirus fiber capsid protein. The fragment according to the present invention comprises the C-terminal knob domain and at least 10 to 100 amino acids of the shaft domain of the adenovirus fiber protein, which is immediately adjacent to the N' terminal end of said knob domain. Preferably, this fragment comprises the C-terminal knob domain and at least 20 to 60 amino acids of the shaft domain of said adenovirus fiber protein.

According to one particular embodiment of this aspect, the DNA construct according to of the present invention comprises nucleic acid sequence coding for the C-terminal knob domain and the adjacent 48 amino acids of the shaft domain of HEV fiber capsid protein. Preferably this sequence is substantially as denoted by SEQ ID NO: 1 or functional homologues and fragments thereof.

In yet another particularly specific embodiment the DNA construct according to of the present invention comprises nucleic acid sequence coding for the C-terminal knob domain and the adjacent 34 amino acids of the shalt domain of EDS fiber capsid protein. Preferably, this sequence is substantially as denoted by SEQ ID NO: 2 or functional homologues and fragments thereof.

In another embodiment the DNA construct according to the invention, wherein said expression vector may be any expression vector, preferably selected from the group consisting of Fowlpox virus, vaccinia virus, Marek disease virus, baculovirus and bacterial yeast and plants plasmids.

One specifically preferred expression vector may be the bacterial plasmid pAL-781 having the restriction map as set forth in FIG. 6. Other preferred expression vectors are the yeast plasmids pPIC3.5K and pHIL-S1. In another preferred embodiment, the expression vector may the Fowlpox virus.

Another aspect relates to a host cell transformed with the DNA construct of the present invention. The host cell according to one embodiment may be any one of prokaryotic and eukaryotic cell. More particularly, the host cell according to the present invention may be any one of bacterial cell, yeast cell, an insect cell or a plant cell. According to one specific embodiment, the host cell of the invention may be an insect cell, preferably, the *Spodoptera frugiperda*. In another embodiment, the host cell of the invention may be a yeast cell, preferably the *Pichia pastoris*. In yet another embodiment, the host cell of the invention may be bacterial cell, preferably *E. coli*.

The host cell according to this embodiment produces the biologically active protein fragment of the invention. Such protein fragment is encoded by the nucleic acid sequence of the invention and elicits protective immunity against a specific adenoviral pathogen, in an animal.

As a fourth aspect, the invention relates to a recombinant protein comprising a fragment of the adenovirus fiber capsid protein. This fragment comprises the C-terminal knob domain and at least 10 to 100 amino acids of the shaft domain immediately adjacent to said knob domain of the adenovirus fiber protein. Preferably, this fragment comprises the C-terminal knob domain and at least 20 to 60 amino acids of the shaft domain of said adenovirus fiber protein.

According to one particular embodiment of this aspect, the recombinant protein of the invention comprises a fragment of the fiber protein of any one of HEV (Hemorrhagic enteritis virus) or EDS (Egg drop syndrome virus).

In specific embodiment, the recombinant protein according to of the present invention comprises the C-terminal knob domain and the adjacent 48 amino acids of the shaft domain of HEV fiber capsid protein. Preferably, this recombinant protein comprises the amino acid sequence substantially as denoted by SEQ ID NO: 3, encoded by the nucleic acid sequence of SEQ ID NO: 1, or functional homologues and fragments thereof.

In yet another specifically preferred embodiment, the adenovirus is EDS (Egg drop syndrome virus). In this embodiment, the recombinant protein of the invention comprises the C-terminal knob domain and the adjacent 34 amino acids of the shaft domain of the EDS fiber capsid protein. Preferably, in this embodiment the amino acid sequence is substantially as denoted by SEQ ID NO: 4, encoded by the nucleic acid sequence of SEQ ID NO: 2 or functional homologues and fragments thereof.

The recombinant protein of the invention is capable of eliciting in an animal protective immunity against a specific viral pathogen. More particularly, the animal may be any one of human and domestic animal.

According to one embodiment, the protein of the invention is capable of eliciting in a domestic animal protective immunity against a specific adenoviral pathogen. Preferably, the domestic animal may be a domestic bird selected from the group consisting of chicken, ducks, geese, quails, pheasants and turkeys. Such adenoviral pathogen according to the invention may be any adenovirus. As a non-limiting example, such adenovirus may be selected from the group consisting of HEV (Hemorrhagic enteritis virus), EDS (Egg drop syndrome virus), Celo and human adenoviruses: serotypes 1-8, 11, 14, 19, 21, 34, 35, 37, 40, 41. Most preferred are the avian adenoviruses HEV and EDS.

In one particular embodiment, the recombinant protein of the invention is capable of eliciting in a turkey protective immunity against a specific adenoviral pathogen, preferably, HEV.

In another particular example, the recombinant protein of the invention is capable of eliciting in a chicken protective immunity against a specific adenoviral pathogen, preferably, EDS virus.

A further aspect of the present invention relates to a vaccinating composition for conferring to an Animal immunity against a pathogenic infection by an adenovirus. This composition comprises as active ingredient an immunologically effective amount of at least one of the recombinant proteins of the invention. This composition may optionally further comprise veterinarily acceptable carrier, adjuvant, diluent and/or excipient.

In one embodiment of the present aspect, the vaccinating composition of the invention may optionally further comprise at least one other protein capable of conferring to an animal immunity against pathogenic infection by another adenovirus.

According to another embodiment, the vaccinating composition of the invention is intended for conferring to an animal immunity against a pathogenic infection by an adenovirus. This composition comprises as active ingredient an immunologically effective amount of at least one of the DNA constructs of the invention. Alternatively, the composition of the invention may comprise as active ingredient an immunologically effective amount of at least one of the nucleic acid sequences of the invention.

The vaccinating composition of the invention is intended for conferring to an animal immunity against a pathogenic infection by any adenovirus. Moreover, this composition is intended to prevent pathogenic infection of an animal by any adenovirus. As non-limiting example, such adenoviral pathogen may be selected from the group consisting of HEV (Hemorrhagic enteritis virus), EDS (Egg drop syndrome virus), Celo and human adenoviruses serotypes 1-8, 11, 14, 19, 21, 34, 35, 37, 40, 41, preferably, HEV and EDS.

The vaccinating composition of the invention is useful for any animal, such as humans or domestic animals. In a preferred embodiment, the composition of the invention is useful for vaccinating domestic animals, preferably, domestic birds. Such domestic birds may be selected from the group consisting of chicken, turkeys, geese, ducks, pheasants, quails, pigeons and ostriches.

According to a specific example, the vaccinating composition of the invention is intended for conferring protective immunity to a turkey against HEV. This composition comprises as active ingredient an immunologically effective amount of at least one recombinant HEV protein or biologically active fragment thereof.

Another specific example is the vaccinating composition according to the invention, for Inferring protective immunity to a chicken against EDS. This composition comprises as active ingredient an immunologically effective amount of at least one recombinant EDS protein or biologically active fragment thereof.

The invention further relates to a method for vaccinating an animal, and preferably a domestic bird, against a pathogenic adenoviral infection. This method comprises administering to said bird an effective immunizing amount of vaccinating composition according to the invention.

Still further, the invention provides for a method for preventing a pathogenic adenoviral infection of an animal, comprising the step of administering to said animal, and preferably to a domestic bird, an effective immunizing amount of vaccinating composition according to the invention.

The methods of the invention may be applicable for vaccinating against any adenovirus. For example, any adenoviral pathogen selected from the group consisting of HEY (Hemorrhagic enteritis virus), EDS (Egg drop syndrome virus), Celo, bovine adenoviruses, canine adenoviruses, any other mammalian adenoviruses and particularly human adenoviruses: serotypes 1-8, 11, 14, 19, 21, 34, 35, 37, 40, 41, preferably, the avian adenoviruses HEV and EDS.

According to specifically preferred embodiment, in cases of HEV infections the method of the invention comprises administering to the bird an effective immunizing amount of vaccinating composition comprising a recombinant HEV protein or biologically active fragments thereof.

According to another specifically preferred embodiment, in cases of EDS infections the method of the invention comprises administering to the poultry an effective immunizing amount of vaccinating composition comprising a recombinant EDS protein or biologically active fragments thereof.

According to the method of the invention, the compositions of the invention may be administered via injection, drinking water, feed, spraying, oral gavage and directly into the digestive tract of said domestic bird.

BRIEF DESCRIPTION OF THE DRAWINGS

The above and other characteristics and advantages of the invention will be more readily apparent through the following examples, and with reference to the appended drawings, wherein:

FIG. 1 Deduced amino acid sequence (SEQ ID NO: 13) and structure of HEV fiber protein. Abbreviations: N' term. (=amino terminal).

DETAILED DESCRIPTION OF THE INVENTION

Figures 2, 3:
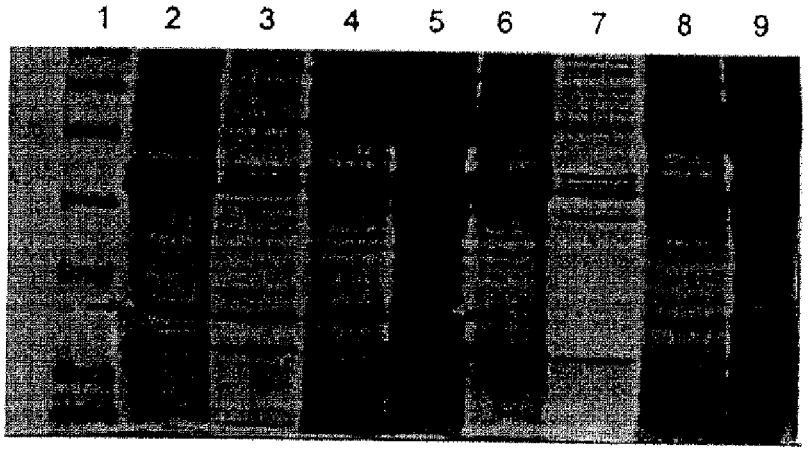
FIG. 2 Release of HEV knob from bacteria and inclusion bodies (i.b) into supernatant. SDS-PAGE stained by Coomassie blue. Molecular size marker (lane 1), Knob in supernatant following release of inclusion bodies (lane 2), Knob in precipitate following release of inclusion bodies (lane 3), Wash solution of i.b that contain knob (lane 4), Supernatant of bacteria that carry the knob gene (lane 5), Supernatant of bacteria that do not carry the knob gene (lane 6), Precipitate after release from i.b from bacteria that do not carry the knob gene (lane 7), Wash solution of i.b that contain knob (lane 8), Supernatant of bacteria that carry the knob gene (lane 9).
FIG. 3 Deduced amino acid sequences, (Shaft: SEQ ID NO: 14; Knob: SEQ ID NO: 15), and structure of EDS fiber protein. Abbreviations: N' term. (=amino terminal).

In a first aspect the present invention relates to a nucleic acid sequence encoding a fragment of the adenovirus fiber capsid protein which fragment is capable of binding to the target cell. The DNA fragment according to the present invention comprises the C-terminal knob domain and at least 10 to 100 amino acids of the shaft domain of the adenovirus fiber protein. As shown by FIG. 1, the shaft domain is immediately adjacent to the N' terminal end of the knob domain.

In one preferred embodiment the nucleic acid sequence of the invention encodes a fragment comprising the C-terminal knob domain and at least 60 amino acids of the shaft domain of said adenovirus fiber protein.

According to another specific embodiment, the nucleic acid sequence according to the invention encodes a fragment of the fiber protein of any one of HEV (Hemorrhagic enteritis virus) or EDS (Egg drop syndrome virus).

A specifically preferred embodiment relates to the nucleic acid sequence according to the invention, wherein said adenovirus is HEV (Hemorrhagic enteritis virus). In this embodiment, the polypeptide fragment encoded by the nucleic acid sequence of the invention comprises the C-terminal knob domain and the adjacent 48 amino acids of the shaft domain of the HEV fiber capsid protein. Preferably, in this embodiment the nucleic acid sequence is substantially as denoted by SEQ ID NO: 1 or functional homologues and fragments thereof.

In another specifically preferred embodiment, the adenovirus is EDS (Egg drop syndrome virus). In this embodiment, the polypeptide fragment encoded by the nucleic acid sequence of the invention comprises the C-terminal knob domain and the adjacent 34 amino acids of the shaft domain of the EDS fiber capsid protein. Preferably, in this embodiment the nucleic acid sequence is substantially as denoted by SEQ ID NO: 2 or functional homologues and fragments thereof.

It is to be appreciated that deletions, insertions, mutations, replacements or modifications of the DNA sequences of the invention, are also contemplated within the scope of the present invention.

A second aspect of the present invention relates to a DNA construct comprising a replicable expression vector and at least one heterologous nucleic acid sequence encoding a fragment of the adenovirus fiber capsid protein. The fragment according to the present invention comprises the C-terminal knob domain and at least 10 to 100 amino acids of the shaft domain of the adenovirus fiber protein, which is immediately adjacent to the N' terminal end of the knob domain. Preferably, this fragment comprises the C-terminal knob domain and at least 20 to 60 amino acids of the shaft domain of said adenovirus fiber protein.

Expression vectors for the production of the molecules of the invention include plasmids, phagemids or other vectors. "Vectors", as used herein, encompass plasmids, viruses, bacteriophages, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. Such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate sites, antibiotic resistance or other markers for election of vector containing cells. Plasmids are the most commonly used form of vector but other forms of vectors which serve an equivalent function and which are, or become known in the art ere suitable for use herein. See, e.g., et al Cloning Vectors. A Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

In general, such vectors contain in addition specific genes, which are capable of providing phenotypic selection in transformed cells. The use of prokaryotic and eukaryotic viral expression vectors to express the nucleic acid sequences coding fore the recombinant proteins of the present invention are also contemplated.

The vector is introduced into a host cell by methods known to those of skill in the art. Introduction of the vector can be accomplished by method that introduces the construct into the cell, including, for example, calcium phosphate precipitation, microinjection, electroporation or transformation. See, e.g., Current Protocols in Molecular Biology, Ausuble, F. M., ed., John Wiley & Sons, N.Y. (1989).

According to one particular embodiment of this aspect, the DNA construct of the invention comprises a nucleic acid sequence coding for the C-terminal knob domain and the adjacent 48 amino acids of the shaft domain of HEV fiber capsid protein. Preferably, this sequence is substantially as denoted by SEQ ID NO: 1 or functional homologues and fragments thereof.

In yet another particularly specific embodiment, the DNA construct of the invention comprises nucleic acid sequence coding for the C-terminal knob domain and the adjacent 34 amino acids of the shaft domain of EDS fiber capsid protein. Preferably, this sequence is substantially as denoted by SEQ ID NO: 2 or functional homologues and fragments thereof.

Functional homologous as used herein mean any sequence variations, mutations deletions and the like, encoding the knob domain and part of the shaft domain of a given adenovirus, in a suitable conformation capable of inducing protective immunity in a vaccinated animal, against pathogenic adenoviral infection.

In another embodiment, the said expression vector may be any expression vector, preferably selected from the group consisting of Fowlpox virus, vaccinia virus, Marek disease virus, baculovirus and bacterial yeast and plants plasmids.

Figure 6:
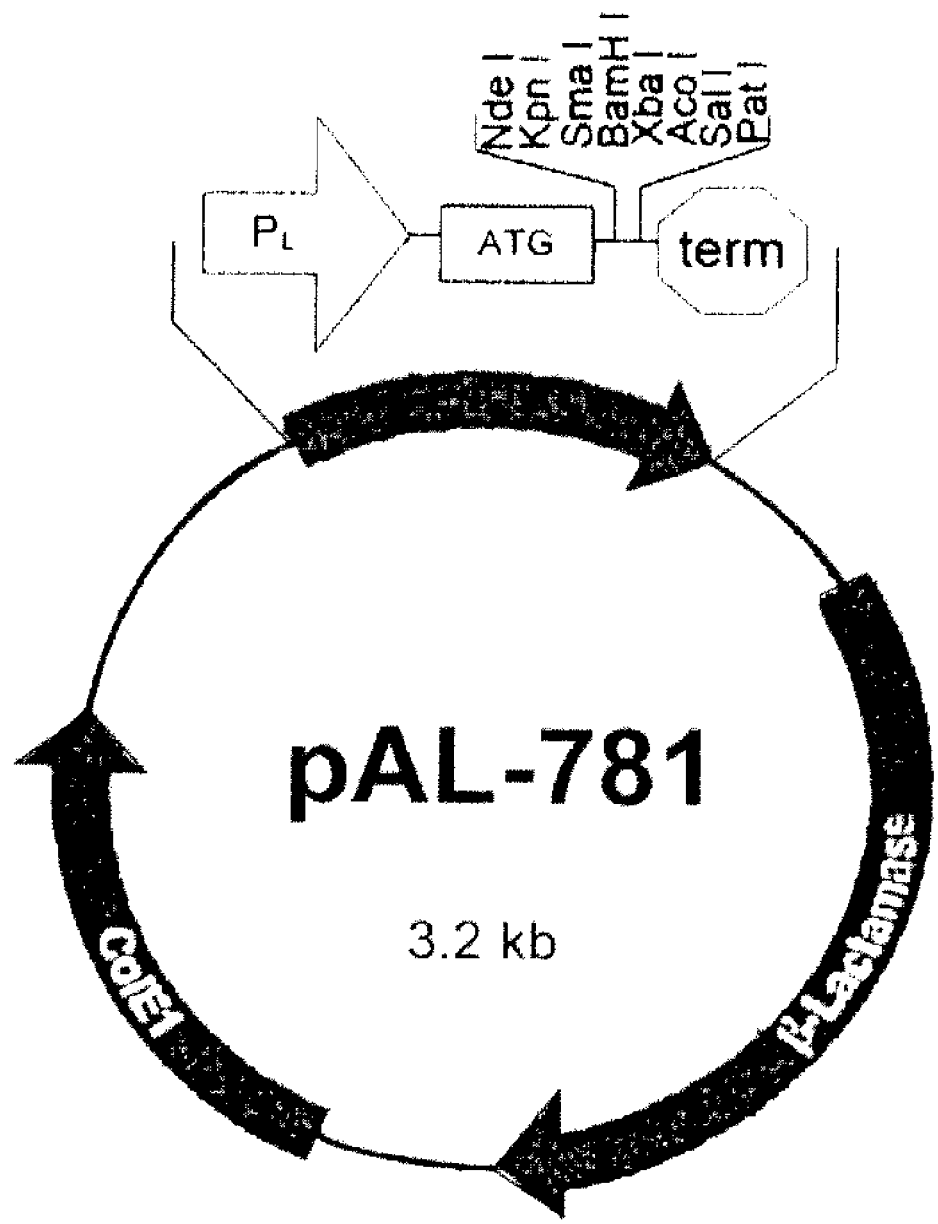
FIG. 6 Map of the pAL-781 plasmid (invitrogene). β-Lactamase: bases 201-1-61, ColE1: bases 1300-1880, PL promoter: bases 2159-2187, Ribosome binding site and ATG: bases 2709-2726, Multiple cloning site: bases 2721.2758, aspA transcription terminator: bases 2759-2825. Abbreviations: term. (=terminator).

One specifically preferred expression vector may be the plasmid pAL-781 having the restriction map as set forth in FIG. 6. Other preferred expression vectors are the yeast plasmids pPIC3.5K and pHIL-S1 (invitrogene). In another preferred embodiment, the expression vector may the Fowlpox virus. Preferred constructs according to the present invention are the HEV knob-s within the pAL-781 plasmid, and the EDS knob-s within the pAL-781 plasmid.

Another aspect relates to a host cell transformed with any one of the DNA constructs of the present invention. Suitable host cells include prokaryotes, lower eukaryotes, and higher eukaryotes. Prokaryotes include gram negative and gram positive organisms, e.g., *E. coli* and *B. subtilis*. Lower eukaryotes include yeast, *S. cerevisiae* and *Pichia*, and species of the genus *Dictyostelium*.

"Host cell" as used herein refers to cell which can be recombinantly transformed with vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cells would be obtained by culturing the cells under conditions which require the induced phenotype for survival.

According to one specific embodiment, the host cell of the invention may be an insect cell, preferably, the *Spodoptera frugiperda*. In another embodiment, the host cell of the invention may be a yeast cell, preferably *Pichia pastoris*. In yet another embodiment, the host cell of the invention may be a bacterial cell, preferably *E. coli*. Among bacterial hosts which may be utilized as transformation hosts, *E. coli* HB2151 cells [k12Δ(lac-pro), ara, nalr, thilF [proAB, lacq, lacZΔM15), (Pharmacia Biotech Inc New Jersey U.S.A)] are particularly useful. Other microbial strains which may be used include other enterobacteria such as *Serratia marcescens*.

The host cells according to the present invention are capable of producing a biologically active protein fragment of the invention. Such protein fragment is encoded by the nucleic acid sequence of the invention and is capable of eliciting in an animal protective immunity against a specific adenoviral pathogen.

As used to describe the present invention, a "pathogen" is a microorganism causing disease in a host. The pathogenic microorganism infects the host animal and the consequence of such infection is deterioration in the health of the host. Pathogenic microorganisms envisioned by the present invention include, but are not limited to, microorganisms such as viruses, preferably, adenoviruses.

In a fourth aspect, the invention relates to a recombinant protein comprising a fragment of the adenovirus fiber capsid protein. This fragment comprises the C-terminal knob domain and at least 10 to 100 amino acids of the shaft domain immediately adjacent to said knob domain of the adenovirus fiber protein. Preferably, this fragment comprises the C-terminal knob domain and at least 20 to 60 amino acids of the shaft domain of said adenovirus fiber protein.

According to one particular embodiment of this aspect, the recombinant protein of the invention comprises a fragment of the fiber protein of any one of HEV (Hemorrhagic enteritis virus) or EDS (Egg drop syndrome virus).

In specific embodiment, the recombinant protein according to the present invention comprises the C-terminal knob domain and the adjacent 48 amino acids of the shaft domain of HEV fiber capsid protein. Preferably, this recombinant protein comprises the amino acid sequence substantially as denoted by SEQ ID NO: 3, encoded by the nucleic acid sequence of SEQ ID NO: 1 or functional homologues and fragments thereof.

In yet another specifically preferred embodiment, the adenovirus is EDS (Egg drop syndrome virus). According to this embodiment, the recombinant protein of the invention comprises the C-terminal knob domain and the adjacent 34 amino acids of the shaft domain of the EDS fiber capsid protein. Preferably, in this embodiment the amino acid sequence is substantially as denoted by SEQ ID NO: 4, encoded by the nucleic acid sequence of SEQ ID NO: 2, or functional homologues and fragments thereof.

The recombinant protein of the invention is capable of eliciting in an animal protective immunity against a specific viral pathogen. More particularly, the animal may be any one of humans and domestic animals.

According to one embodiment, the protein of the invention is capable of eliciting in a domestic animal protective immunity against a specific adenoviral pathogen. Preferably, the domestic animal may be a domestic bird selected from the group consisting of chicken, ducks, geese, quails, pheasants and turkeys. Such adenoviral pathogen according to the invention may be any adenovirus. As a non-limiting example, such adenovirus may be selected from the group consisting of HEV (Hemorrhagic enteritis virus), EDS (Egg drop syndrome virus), Celo and human adenoviruses: serotypes 1-8, 11, 14, 19, 21, 34, 35, 37, 40, 41. Most preferred are the avian adenoviruses HEV and EDS.

In one particular embodiment, the recombinant protein of the invention is capable of eliciting in a turkey protective immunity against a specific adenoviral pathogen, preferably, HEV.

In another particular example, the recombinant protein of the invention is capable of eliciting in a chicken protective immunity against a specific adenoviral pathogen, preferably, EDS virus.

A process for the production of the recombinant protein or peptide of the invention is also within the scope of the invention. The process comprises the steps of (a) transforming a host cell with the nucleotide sequence of the invention or transfecting a host cell with a DNA construct of the invention; (b) culturing the cells obtained in (a) under conditions in which expression of the protein takes place; and (b) isolating the expressed recombinant protein or peptide from the cell culture or/and the culture supernatant. Evidently, the suitable means to perform such steps are well know to the man of ordinary skill in the art [ThioFusion on Expression Systems Version 1.1 Invitrogen Corporation San Diego, Calif. (1995); *Pichia* Expression Kit, Version 1.8, Invitrogen Corporation San Diego, Calif. (1995); and Pitcovski J. et. al. Avian Disease 40:75-761 (1996)].

A further aspect of the present invention relates to a vaccinating composition for conferring to an animal immunity against a pathogenic infection by an adenovirus. This composition comprises as active ingredient an immunologically effective amount of at least one of the recombinant proteins of the invention. This composition may optionally further comprise veterinarily acceptable carrier, adjuvant, diluent and/or excipient.

As used herein, "effective amount" means an amount necessary to achieve a selected result. For example, an effective amount of the composition of the invention is an amount which confers immunity against pathogenic viral infections.

The vaccinating compositions of the invention generally comprise a buffering agent, an agent which adjusts the osmolarity thereof, and optionally, one or more pharmaceutically or veterinarily acceptable carriers, excipients and/or additives or adjuvants as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable or mineral oils. The proper fluidity can be maintained, for example, by the use of a coating, such as lecithin, by the maintenance of the required particle size in, the case of dispersion and by the use of surfactants.

Similarly, one of skill in the art may readily select other desired components for inclusion in a vaccinating composition of the invention, and such components are not a limitation of the present invention.

As used herein "pharmaceutically or veterinarily acceptable carrier" includes any and all solvents, dispersion media, coatings, antibacterial and anti-fungal agents and the like. The use of such media and agents for pharmaceutical active substances is well known in the art. Except as any conventional media or agent is incompatible with the active ingredient, its use in the veterinary therapeutic composition is contemplated.

Therapeutic formulations may be administered in any conventional dosage formulation. Formulations typically comprise at least one active ingredient, as defined above, together with one or more acceptable carriers thereof.

Each carrier should be pharmaceutically and veterinarily acceptable in the sense of being compatible with the other ingredients and not injurious to the treated animal. The formulations may conveniently be presented in unit dosage form and may be prepared by any methods well known in the art of pharmacy and veterinary.

The composition of the invention may be mixed with nutritive feed material or water supplies for the animal. It is contemplated however that the effective composition can either be mixed with the nutritive feed material or water or fed to the animal separately. The effective composition must be provided in an amount effective to confer immunity to an animal and preferably to a domestic bird, against infection caused by a virus. This amount will vary depending upon the size of for example, the domestic bird. Small birds, such as pigeons will require smaller quantities of the effective composition than, for example, turkeys, to vaccinate against viral pathogenic infection. Effective amount can readily be determined by the skilled veterinarian.

In one embodiment of the present aspect, the vaccinating composition of the invention may optionally further comprise at least one other protein capable of conferring to an animal immunity against pathogenic infection by another adenovirus.

According to another embodiment, the vaccinating composition of the invention is intended for conferring to an animal immunity against a pathogenic infection by an adenovirus. This composition comprises as, active ingredient an immunologically effective amount of at least one of the DNA constructs of the invention. Alternatively, the composition of the invention may comprise as active ingredient an immunologically effective amount of at least one of the nucleic acid sequence of the invention.

The vaccinating composition of the invention is intended for conferring to an animal immunity against a pathogenic infection by any adenovirus. As a non-limiting example, such adenoviral pathogen may be selected from the group consisting of HEV (Hemorrhagic enteritis virus), EDS (Egg drop syndrome virus), Celo and human adenoviruses: serotypes 1-8, 11, 14, 19, 21, 34, 35, 37, 40, 41, preferably, the avian adenoviruses HEV and EDS.

The vaccinating composition of the invention is applicable for any animal such as human or domestic animal. In a preferred embodiment, the composition of the invention is useful for vaccinating domestic animals, preferably, domestic birds. Such domestic birds may be selected from the group consisting of chicken, turkeys, geese, ducks, pheasants, quails, pigeons and ostriches.

According to a specific example, the vaccinating composition of the invention is intended for conferring to a turkey protective immunity against HEV. This composition comprises as active ingredient an immunologically effective amount of at least one recombinant protein comprising the HEV sequences.

Another specific example is the vaccinating composition for conferring to chicken protective immunity against EDS. This composition comprises as active ingredient an immunologically effective amount of at least one recombinant protein of the invention comprising EDS sequences.

It is to be appreciated that the compositions of the invention are intended for prevention of adenoviral pathogenic infection of an animal.

The invention further relates to a method for vaccinating an animal, and preferably a domestic bird, against a pathogenic adenoviral infection. This method comprises administering to the birds an effective immunizing amount of a vaccinating composition of the invention.

The method of the invention may be applicable for vaccinating against any adenovirus and moreover, for preventing a pathogenic infection of any adenovirus, for example, an adenoviral pathogen selected from the group consisting of HEV (Hemorrhagic enteritis virus), EDS (Egg drop syndrome virus), Celo and human adenoviruses: serotypes 1-8, 11, 14, 19, 21, 34, 35, 37, 40, 41, preferably, the avian adenoviruses HEV and EDS.

According to specifically preferred embodiment, in cases of HEV infections, the method of the invention comprises administering to the poultry an effective immunizing amount of a vaccinating composition comprising a recombinant protein comprising HEV sequences.

According to another specifically preferred embodiment, in cases of EDS infections, the method of the invention comprises administering to the poultry an effective immunizing amount of vaccinating composition comprising a recombinant protein comprising EDS sequences.

According to the method of the invention, the compositions of the invention may be administered via injection, drinking water, feed, spraying, oral gavage and directly into the digestive tract of said domestic bird.

The vaccinating compositions of the invention are administered and dosed in accordance with good veterinary practice, taking into account the clinical condition of the individual animal, the site and method of administration, scheduling of administration, the animal's age, body weight, diet and other factors, well known to the veterinary practitioner. The doses may be single doses or multiple doses and the treatment may be effected at any age and even in ovo.

Any conventional method for administering the products of the invention (e.g. the DNA sequences, the DNA constructs, or the protein or peptide product of the invention), such as tablets, suspensions, solutions, emulsions, capsules, powders, syrups, and the like may be used, as long as the biological activity of the therapeutic ingredient thereof is retained.

Administration may be oral, subcutaneous or parenteral, including intravenous, intramuscular, intradermal, intraperitoneal and intranassal administration as well as intrathecal and infusion techniques. Nevertheless, most preferred methods are oral administration and injection. Following injection, the DNA construct of the invention will circulate until it recognizes the host cell with the appropriate target specificity for infection.

The pharmaceutical forms suitable for injection use include sterile aqueous solutions, water-in-oil or oil-in-water emulsions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The prevention of the action of microorganisms can be brought about by various antibacterial and anti-fungal agents, for example, parabens, chlorobutanol, phenol, sorbic acid, thimerosal, formaldehyde and the like. In many cases, it will be preferable to include isotonic agents, for example, sugars or sodium chloride.

Sterile injectable solutions are prepared by incorporating the vaccinating composition in the required amount into the appropriate solvent with various of the other ingredients enumerated above, as required, followed by filtered sterilization or emulsification. Generally, dispersions are prepared by incorporating the various sterilized active ingredients into a sterile vehicle which contains the basic dispersion medium and the required other ingredients from those enumerated above.

A number of methods of the art of molecular biology are not detailed herein, as they are well known to the person of skill in the art. Such methods include site-directed mutagenesis, PCR cloning, expression of cDNAs, analysis of recombinant proteins or peptides, transformation of bacterial and yeast cells, transfection of mammalian cells, and the like. Textbooks describing such methods are e.g., Sambrook et al., Molecular Cloning A Laboratory Manual, Cold Spring Harbor Laboratory; ISBN: 0879693096, 1989, Current Protocols in Molecular Biology, by F. M. Ausubel, ISBN: 047150338X, John Wiley & Sons, Inc. 1988, and Short Protocols in Molecular Biology, by F. M. Ausubel et al. (eds.) 3rd ed. John Wiley & Sons; ISBN: 0471137812, 1995. These publications are incorporated herein in their entirety by reference. Furthermore, a number of immunological techniques are not in each instance described herein in detail, as they are well known to the person of skill in the art. See e.g., Current Protocols in Immunology, Coligan et al. (eds), John Wiley & Sons. Inc., New York, N.Y. All of the other publications referred to herein are also incorporated by reference in their entirety, including publications cited therein.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It must be noted that, as used in this specification and the appended claims, the singular forms "a", "an" and "the" include plural referents unless the content clearly dictates otherwise.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

The following examples are thus only representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Viruses
HEV—cat 821500 ABIC ISRAEL
EDS—76 strain, ABIC ISRAEL.
Bacteria/Strains
GI698 E. coli cells (invitrogen cat. No. K350-01)
JM109 E. coli cells (PROMEGA cat. No. 1352391).
Vaccine
EDS-inactivated strain EDS 76, ABIC ISRAEL
HE-inactivated local strain, ABIC ISRAEL
Vectors
pAL-781, the map is shown in FIG. 6 (Invitrogen cat. no. k1710-01).
pHIL-S1 (Invitrogen cat. no. k1710-01).
pPIC3.5K (Invitrogen cat. no. k1710-01).
pQE30 (QIAGEN cat. no. 33303)
Isolation of Virus (HEV or EDS)
Turkeys were exposed to the virulent strain of HEV. Five days later, birds were sacrificed and the spleens removed.

Distilled water, twice the volume of the tissue, was added and the spleens were ground and homogenized for 5 min. To rupture the cells, the tissue homogenate was frozen and thawed three times at −70° C. and 30° C., respectively, followed by centrifugation at 10,000×g, 4° C. for 20 minutes. The supernatant was mixed with trichloro-trifluoroethane (1:3) and centrifuged at 5000×g, 4° C. for 30 minutes. The supernatant was collected and added on top of the following gradient: 12 ml of 46.2% (w/v) cesium chloride (CsCl) (density of 1.35 g/ml); 12 ml of 36% (w/v) CsCl (density of 1.24 g/ml); 6 ml of 1M sucrose. The gradient was centrifuged for 24 hrs at 85,000×g, 4° C., with SW28 rotor. The virus was isolated from a white ring that was formed between the two CsCl layers. The virus band was collected, diluted in Tris EDTA (TE), and re-pelleted by centrifugation at 26000×RPM for 2 hrs. The pellet was collected, re-suspended in distilled water and dialyzed against TE. HEV proteins were identified by SDS-PAGE. The virus was stored at −20° C. until used. The EDS virus was isolated similarly from amnio-allantoic fluid of 12-days-old EDS-infected embryonated duck eggs.

Purification of Viral DNA

The virus (isolated as described herein above) was incubated for 3 hrs in a solution containing 0.01M Tris, 0.01M NaCl, 0.01M EDTA, 0.5% SDS, and 50 µg/ml proteinase K. The supernatant was collected, added to a solution containing phenol:chloroform:isoamyl-alcohol (1:1:0.25, v/v) and mixed vigorously for 30 s. After centrifugation at 18000×g 4° C. for 5 min, the supernatant was collected and viral DNA was precipitated by incubating for 20 min at −70° C. 1/10 the volume of 2 M NaCl and 2 volumes of 100% ethanol. Following centrifugation, the pellet was washed in a similar volume of 70% ethanol and re-centrifuged. The supernatant was discarded and the pellet, containing the DNA, was air-dried. The DNA was electrophoresed on a 0.8% agarose gel. The viral DNA was visualized by ethidium bromide staining.

Preparation of Recombinant Proteins

DNA sequences encoding the hexon, fiber were prepared by performing PCR reaction using the following primers:
5' primer for the Fiber construct
5' gcg ggt acc t atg cta cac cat cac cat cac aag cga cta cgg ttg gac 3', also denoted as SEQ ID NO. 9.
3' primer for the Fiber construct
5' atc tot aga cta ctg tgc tcc aac ata tg 3', also denoted as SEQ ID NO. 10.
5' primer for the Hexon construct
5' cgg ggt acc tct gga acc cca acg tg 3', also denoted as SEQ ID NO. 11.
3' primer for the Hexon construct
5' gc tct aga tca tgt tgc tgc act acc 3', also denoted as SEQ ID NO. 12.

The resulting PCR products were sub-cloned into pAL plasmid and the recombinant proteins were expressed in *E. coli*.

Dissolving Recombinant Protein from Inclusion Bodies

Lysis of transformed bacteria and release of the recombinant protein to supernatant was performed as described in literature [S. Doonan, Protein Purification Protocols, 59:33-37 (1998)]. Bacteria were treated with lysozyme, and the inclusion bodies were dissolved in 8M Urea, 50 mM Tris-HCl, 50 mM NaCl, 1 mM EDTA.

Recombinant proteins were optionally recovered as soluble proteins in PBS following dialysis.

ELISA

Antigens for ELISA were diluted in coating buffer (e.g. 0.05M carbonate-bicarbonate, pH=9.6), and polystyrene microliter plates were coated with the antigens by incubation for 1 hr at 37° C. or overnight at 4° C. The antisera were diluted 1:200 by PBS with 0.1% BSA. The plates were rinsed with PBS containing 0.05% Tween 20, the sera were added to the antigen coated wells in duplicates or triplicates. After two hours at 37° C., the plates were rinsed again, and rabbit anti-chicken immunoglobulin conjugated to alkaline phosphatase [Sigma] was added. The plates were then incubated for two hours at 37° C. and rinsed again. Then a substrate, nitrophenyl phosphate, was added. The color of the solution changed to yellow in proportion to the amount of birds antiviral antibodies. Light absorbancy was read in SLT spectra ELISA reader [Lumitron].

SDS PAGE and Western Blotting

For acrylamide gel electrophoresis (PAGE) and Western blotting, the protein preparations were boiled for 3 min. in a sample buffer containing 3% sodium dodecyl sulfate (SDS) and 5% mercaptoethanol. Polypeptides were analyzed in 12% w/v polyacrylamide slab gels, using the discontinuous SDS gel system (Laemmli, U.K., Nature, 227 (1970) 680-685). In most cases, two slab gels were electrophoresed simultaneously. One was stained with Coomassie Brilliant Blue R, and the proteins from the second were electrotransferred on to nitrocellulose filter using a semi-dry system [bio rad]. The filters were cut into strips 5 mm (each with a different sample), and then incubated separately in the relevant sera diluted 1:200. After several washes in PBS, the filters were incubated with rabbit anti-chicken IgG-peroxidase conjugate (Sigma) diluted 1:1000, followed by incubation in the substrate solution (Sigma), 3,3'-diaminobenzidine.

Vaccination with Recombinant Proteins

The different recombinant EDS or HEV proteins, the inactivated viruses as positive controls and PBS as a negative control, were emulsified in mineral oil (Marcol 52, Esso, France) to form a 20% water-in-oil emulsion or in FCA or FIA (Freund Complete or Incomplete Adjuvant). All recombinant proteins were injected at 50 µg per bird in a volume of 500 µl. The emulsions were produced by a polytron apparatus (Kinematics, Kriens, Switzerland). These emulsions were injected intramuscularly into SPF (specific pathogen free) or commercial chickens, at the age of 3.5 to 6.5 weeks, or to turkeys at the age of 3-6 weeks. All birds were grown in isolation units from 1 day of age.

Hemagglutination Inhibition (HI) Test

EDS fiber protein causes agglutination of red blood cells, whereas antibodies against this protein inhibit this hemagglutination. This phenomenon is used to measure the efficiency of a vaccine. The test was performed against 4 hemagglutination activity (HA) units of egg-propagated EDS virus in a 96-well microtiter plate and expressed as log 2 geometric mean titer.

Virus Neutralization Test

The serum neutralization (SN) test checks the ability of antibodies produced against an antigen to prevent the penetration and propagation of a virus in cells. The sera of each group were pooled and filtered through 0.2 micron filter. EDS virus ($10^{6.4}$ EID50/ml) was incubated for 30 min at 37° C. with an equal volume of filtered sera. The mixtures were inoculated into the allantoic cavity of six embryonated duck eggs 12 day-old which were then incubated for 7 more days and candled daily. At the end of the incubation period viral propagation was evaluated by testing hemagglutination activity (HA) in the amnio-allantoic fluid. Results are expressed as percent eggs in which the virus was neutralized. Anti ND antibodies, as a negative control, caused no SN. Anti EDS antibodies, as a positive control, caused 100% serum neutralization.

Agar Gel Precipitation (AGP) Test

The test was carried out as described by Domermuth C. H. and Gross W. B. [In: Swayne D. H. editor: A Laboratory Manual for the Isolation and Identification of Avian Pathogens. Fourth edition, American association of Avian Pathologists, Kennet Square, Pa., USA, 1998: 106-110]. Briefly, agar was poured onto glass slides, after solidifying holes of 2 mm diameter were cut. Antigen, consisted of a 1:2 dilution w/v of spleen extract from HEV-infected turkeys, was put in the central well and sera samples in the peripheral wells. For detection of antigen in spleens after challenge—positive serum was placed in the central well and spleens extracts in the peripheral wells.

Example 1

Creation of the HEV Knob-s Recombinant Protein

The amino acid sequence of the HEV fiber protein may be divided into three parts as shown in FIG. 1, the amino terminal domain, the shaft domain and the knob domain. The carboxy-terminal part, referred to as "knob", binds to target cells.

The present inventors have speculated that in order to create an efficient vaccine against the HEV, it would be advantageous to direct creation of antibodies to a specific domain of the fiber protein, the "knob", which binds to the target cell. To enable folding of the "knob" recombinant protein in the correct conformation, 48 amino acids from the adjacent "shaft" domain of the fiber protein were added to the knob domain.

The DNA sequence that codes for the knob part of HEV fiber and adjacent 48 amino acids of shaft was isolated by PCR using as primers the sequences as denoted by SEQ ID NO: 5, 6, HEV DNA was used as a template. The PCR product was cloned into the XbaI/KpnI site of the pAL plasmid (Invitrogen). *E. coli* cells were transformed with pAL plasmid that carried the knob (pAL-knob). Colonies that carried the desired gene were identified and tested by PCR. The sequence of the DNA at the 5' end was determined and was found to be in the correct reading frame.

For production of the HEV fiber knob-s recombinant protein, transformed *E. coli* colonies were grown overnight and induced by tryptophane. Bacteria were disrupted by sonication and the products were tested by SDS-PAGE. Identity of the desired recombinant HEV fiber knob-s protein was verified by western blot analysis using anti HEV antibodies. The recombinant protein was dissolved from inclusion bodies as described in the experimental procedures, prior to its injection (FIG. 2).

Example 2

Protection of Turkeys Against Virulent HEV by Recombinant Knob Vaccination

Efficiency of the vaccinating composition of the invention against a virulent HE virus was next tested. Thirty turkeys, in isolation units, were divided into three groups, and were injected twice intramuscularly with different antigens emulsified in Freund's Incomplete Adjuvant—1.0 ml per bird. The first injection took place at the age of four weeks and the second one at the age of 7 weeks. The birds were bled two weeks after the second inoculation (5 weeks after the first vaccination), and checked for the presence of antibodies by the Agar Gel Precipitation (AGP) test. All birds were challenged with virulent HEV and sacrificed four days later. Resistance to challenge was determined by detecting the presence or absence of HE virus in spleens of the tested birds by the AGP method, absence of virus indicates resistance of the turkey to HEV. Group one was inoculated with recombinant HEV fiber knob-s; group two was inoculated with the commercial vaccine of killed HEV virus DAMN (BLT, Abic, Israel) as positive control; and group three with PBS buffer as negative control. Specificity of antibodies was determined by Western blot of serum proteins. As shown by Table 1, the results indicate that the HEV fiber knob-s recombinant protein of the invention, acts as a significantly efficient vaccine by protecting 100% of the vaccinated birds. Furthermore, Table 1 shows that the HEV fiber knob-s of the invention is even more efficient than the commercial vaccine.

TABLE 1

| HEV fiber knob-s as protecting vaccine | |
|---|---|
| Group | No. of Protected birds |
| 1. HEV fiber knob-s | 10/10 |
| 2. Positive control (commercial vaccine) | 8/9 |
| 3. Negative control (PBS buffer) | 4/10 |

Example 3

Recombinant HEV Fiber Knob-s Prepared as Inclusion Bodies, Efficiently Protects Vaccinated Birds In order to further optimize the vaccinating composition of the invention, immunization of birds using HEV-Fiber knob-s recombinant protein prepared by different procedures, was next performed. Forty turkeys in isolation units, at the age of four weeks, were divided into five groups of eight birds each. The turkeys were injected once intramuscularly with antigens prepared and extracted using different procedures, or with controls, emulsified as water-in-oil emulsion (1.0 ml per bird). All birds were challenged three weeks after vaccination with virulent HEV and sacrificed four days later. Resistance to challenge was determined by detecting the presence or absence of HE virus in spleens of the tested birds by the AGP method. One group was inoculated with recombinant HEV fiber knob-s prepared as inclusion bodies, the second group was inoculated with recombinant HEV fiber knob-s prepared using urea (for inclusion bodies extraction) and dialysis, the third group was inoculated with the commercial vaccine of killed HEV virus DAMIN (BLT, Abic, Israel) as positive control, the fourth group served as a negative control and was inoculated with preparation of the empty plasmid (pQE30) and the fifth group which also served as a negative control, was inoculated with PBS buffer. Specificity of antibodies was determined by Western blot of serum proteins. As shown by Table 2, the HEV fiber knob-s recombinant protein prepared as inclusion bodies, acts as a significantly efficient vaccine by protecting 100% of the vaccinated birds. However, HEV fiber knob-s recombinant protein extracted from inclusion bodies using urea and dialysis led only to 50% protection (4 out of 8 birds). Vaccination with the commercial vaccine yielded only 75% protection (6 out of 8). As expected, vaccination with both negative controls had no protective effect. These results indicate that the HEV fiber knob-s of the invention used as inclusion bodies is more efficient than the commercial vaccine. Moreover, the efficient use of the HEV fiber knob-s recombinant protein of the invention as a crud preparation (inclusion bodies) indicates that in addition to safety and increased efficiency as a protecting vaccine, this vaccinating composition may be even less expensive compared to commercially available vaccines.

TABLE 2

HEV fiber knob-s as protecting vaccine

| Group | No. of Protected birds |
|---|---|
| HEV fiber knob-s (inclusion bodies) | 8/8 |
| HEV fiber knob-s (urea + dialysis) | 4/8 |
| Positive control (commercial vaccine) | 6/8 |
| Negative control (pQE30 without HEV fiber knob-s) | 1/8 |
| Negative control (PBS buffer) | 0/8 |

Example 4

Creation of the EDS Knob-s Recombinant Protein

Similarly to HEV, the amino acid sequence of the EDS fiber protein may be divided into three parts as shown in FIG. 3, the amino terminal domain, the shaft domain and the knob domain which binds to the target cell.

To create an efficient vaccine against the EDS, a recombinant EDS fiber knob-s protein was designed, similarly to the HEV fiber knob-s (described above). To enable folding of the "knob" recombinant protein in the correct conformation, 34 amino acids from the adjacent "shaft" domain of the fiber protein were added to the knob domain.

The DNA sequence that codes for the knob part of EDS fiber and adjacent 34 amino acids of shaft was isolated by PCR using primers as denoted by SEQ ID NO: 7 and 8 (sequence listing), EDS DNA was used as a template. The PCR product was cloned into KpnI and XbaI sites in the pAL plasmid and recombinant plasmid was transformed into GI698 E. coli cells (Invitrogen) according to kit instruction. Colonies that carried the desired gene were identified and tested by PCR and by analysis with restriction enzymes. The sequences of two of the colonies were determined and the reading frame and the gene were found to be correct.

Figure 4:
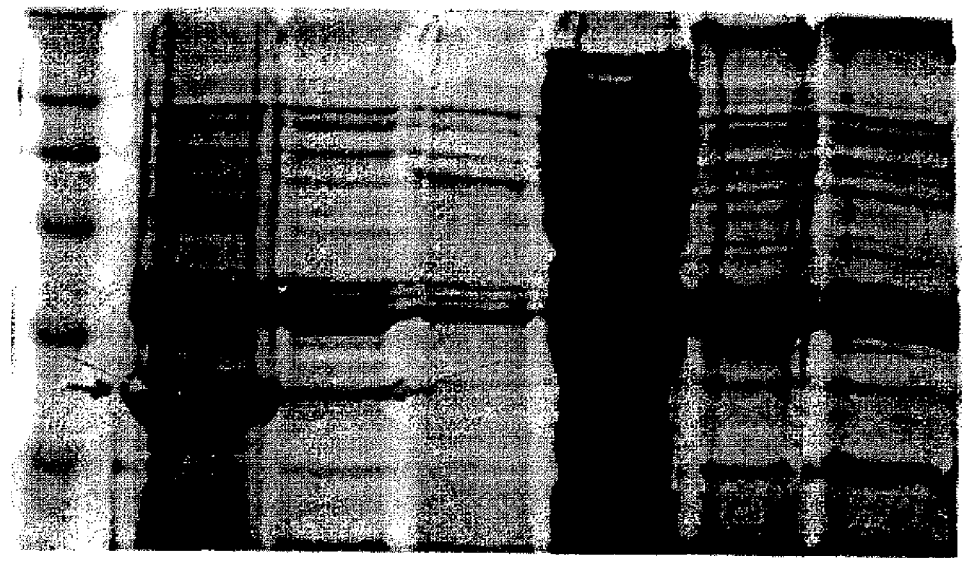
FIG. 4 SDS-PAGE stained with coomassie blue to test the release of the E-knob-s into solution. Molecular size marker (lane 1), E-knob-s released into solution (lane 2), Residual precipitate (lane 3), Wash solution of inclusion bodies (lane 4), Lysis solution of bacteria with E-knob-s (lane 5), Lysis solution of bacteria with plasmid without insert (lane 6), Precipitate of bacterial lysis that carry plasmid without insert (lane 7).

One liter of induction medium was inoculated by a transformed colony of E. coli. Expression induced by tryptophan and cells were harvested after three hours. Bacteria were disrupted by sonication and centrifuged. Inclusion bodies were dissolved as described in the experimental procedures. The recombinant protein was characterized by SDS-PAGE and as expected, the size of knob-s was 28 kD (FIG. 4).

Example 5

Vaccination with Recombinant EDS Proteins

Fiber protein of EDS causes agglutination of red blood cells, whereas antibodies against the fiber protein inhibit this haemagglutination. These phenomena can be used for measuring efficiency of the vaccination. In addition, serum neutralization test (SN) checks the ability of antibodies produced against an antigen, to prevent the penetration and propagation of a virus in cells.

Therefore, three different EDS recombinant proteins, Heron, Fiber and the recombinant protein of the invention, Fiber knob-s (that were prepared as described in experimental procedures), as well as a commercial vaccine as a positive control [inactivated strain EDS 76, ABIC ISRAEL] were injected twice (first injection at the age of 3.5 weeks and the second at 7.5 weeks) to Specific Pathogen Free (SPF) chicken, and the efficacy of protection was tested by haemagglutination inhibition and serum neutralization tests, as described above.

The fiber protein induced production of antibodies that cause HI [haemagglutination inhibition], when injected by itself or in combination with recombinant hexon. However, in the form of inclusion bodies, the fiber protein did not yield HI antibodies.

Sera for the HI test were tested 3 and 5 weeks after first vaccination. As shown in Table 3, results of the haemagglutination inhibition test showed that EDS fiber knob-s [E-knob-s] induced high levels of HI antibodies particularly as compared to hexon and fiber that induced lower levels of HI antibodies.

For the serum neutralization test, sera taken five weeks after vaccination from birds of the different test groups, were incubated with the EDS virus. This mixture was then inoculated into the allantoic cavity of six 12-days-old embryonated duck eggs as described. As shown by Table 3 (column SN), the anti EDS fiber knob-s and the positive control [commercial vaccine] showed 100% neutralization of the virus. Anti-hexon and anti-fiber antibodies showed a very weak serum-neutralization effect.

TABLE 3

Efficiency of recombinant proteins in haemagglutination inhibition test and in serum neutralization test

| Vaccine | HI antibodies | | SN |
|---|---|---|---|
| | 3 wk | 5 wk | % neut. |
| Hexon | 1.9 | 4.7 | 16 |
| Fiber | 3.1 | 6.3 | 33 |
| E-knob-s | 8.1 | 9.7 | 100 |
| EDS | 8.6 | 11.3 | 100 |
| Unvac. | 2.6 | 3.3 | 33 |

Figure 5:
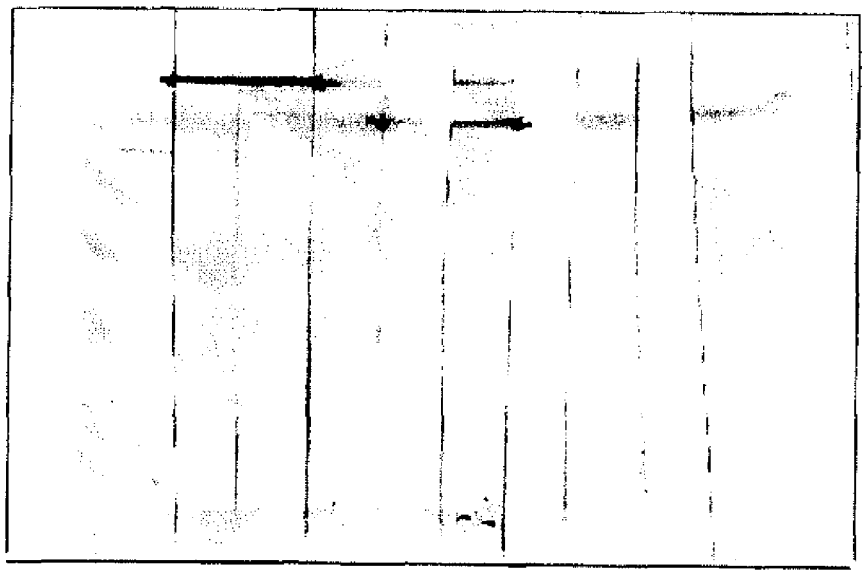
FIG. 5 Immunoblot testing the production of anti-EDS antibodies in response to vaccination with various antigens. Nitrocellulose strips containing whole EDS virus extract were incubated with serum of birds that were vaccinated with the following different antigens: commercial anti-EDS (lane 2), pool of 12 sera 21 days post vaccination of birds injected with hexon (lane 3), Pool of 12 sera 35 days post vaccination of birds injected with hexon (lane 4), Pool of 12 sera 21 days post vaccination of birds injected with fiber (lane 5), Pool of 12 sera 21 days post vaccination of birds injected with E-knob-s (lane 6), Pool of 12 sera 35 days post vaccination of birds injected with E-knob-s (lane 7), Pool of 12 sera 21 days post vaccination of unvaccinated birds (negative control) (lane 8), Pool of 12 sera 35 days post vaccination of unvaccinated birds (negative control-lane 9), Pool of 12 sera 21 days post vaccination of birds injected with commercial vaccine (lane 10), Pool of 12 sera 35 days post vaccination of birds injected with commercial vaccine (lane 11), molecular size marker is shown in lane 1.

Antibodies created in the sera of birds that were vaccinated with different recombinant proteins, were further analyzed by Western blot (FIG. 5). Whole virus was used as antigen, and the nitrocellulose strips were incubated with pools of serum obtained from the different test groups. As shown by FIG. 5, birds that were vaccinated with whole EDS virus extract or recombinant antigens of the virus produced in E. coli, developed antibodies which recognize the viral proteins on the Western blot strip, at the expected size.

Thus, vaccinating birds using the knob-s recombinant protein of the invention induced production of specific antibodies against EDS virus. Moreover, use of the partial recombinant fiber protein (knob-s) of the invention, was significantly more efficient than the whole fiber protein (Table 3).

Example 6

The EDS Knob-s Recombinant Protein of the Invention Efficiently Vaccinate Commercial Birds Using One Injection The efficiency of EDS vaccinating composition of the invention, as well as different procedures of preparation were further analyzed by vaccinating commercial light breed chickens (Hafetz Haim hatchery, ISRAEL) placed at 1 day of age in isolation units.

Five groups of twelve 4 weeks old commercial chickens each were injected once with the following antigens: birds in group one were injected with the EDS Fiber knob-s recombinant protein (50 μg/bird) prepared using urea without dialysis (inclusion bodies were dissolved using 8M urea as indicated in experimental procedures), birds in group two were injected with EDS Fiber knob-s recombinant protein (50 μg/bird) prepared using urea with dialysis, birds in group three were injected with recombinant protein isolated from the sonicated bacteria as a pellet of inclusion bodies, birds of group four were injected with commercial vaccine as a positive control and the fifth group served as negative control (un-injected). Sera of the vaccinated birds from the different test groups were tested 3 and 5 weeks after vaccination, by HI and SN (using 12 days old duck eggs, as described in experimental procedures).

As shown by Table 4, vaccination using the EDS Fiber knob-s recombinant protein prepared using urea and dialysis (group two), induced efficient production of antibodies, as was shown by both HI and SN tests, 3 and 5 weeks post vaccination. However, vaccination with preparation of recombinant protein without dialysis (group one), showed low creation of antibodies as indicated by the HI test and no serum inhibition (the SN test). These results indicate that in the presence of urea, the conformation of the recombinant protein is less immunogenic. Interestingly, the vaccinating preparation bodies (group three) induced efficient production of antibodies, as revealed by HI test performed 3 and 5 weeks post vaccination, however, these antibodies were less efficient in the SN test (33% and 66% inhibition 3 and 6 weeks post vaccination, respectively).

In summary, the EDS Fiber knob-s recombinant protein of the invention can efficiently vaccinate commercial birds even following only one vaccination.

TABLE 4

Efficiency of different preparations of the recombinant proteins in vaccinating commercial birds as indicated by haemagglutination test and serum neutralization test

| | HI | | | |
| --- | --- | --- | --- | --- |
| | antibodies | | SN % neut | |
| Vaccine | 3 wk | 5 wk | 3 wk | 5 wk |
| 1. E-knob-s + urea | 2.9 | 3.8 | 0 | 0 |
| 2. E-knob-s + urea + dialysis | 6.8 | 5.6 | 100 | 100 |
| 3. E-knob-s-inclusion bodies | 6.1 | 5.9 | 33-50 | 66-100 |
| 4. EDS | 6.1 | 6.4 | 100 | 100 |
| 5. Unvac. | 0.9 | 0 | 16 | 0 |

The invention claimed is:

1. A recombinant protein which consists of the C-terminal knob domain and the adjacent 48 amino acids of the shaft domain of the HEV fiber capsid protein, as denoted by SEQ ID NO: 3, or which consists of the C-terminal knob domain and the adjacent 34 amino acids of the shaft domain of the EDS fiber capsid protein, as denoted by SEQ ID NO: 4.

2. The recombinant protein of claim 1, which consists of the C-terminal knob domain and the adjacent 48 amino acids of the shaft domain of the HEV fiber capsid protein, as denoted by SEQ ID NO: 3.

3. The recombinant protein of claim 1, which consists of the C-terminal knob domain and the adjacent 34 amino acids of the shaft domain of the EDS fiber capsid protein, as denoted by SEQ ID NO: 4.

4. A composition comprising an immunologically effective amount of the recombinant protein of claim 1, and a veterinarily acceptable carrier, adjuvant, diluent and/or excipient.

5. The composition of claim 4, wherein the recombinant protein consists of the C-terminal knob domain and the adjacent 48 amino acids of the shaft domain of the HEV fiber capsid protein, as denoted by SEQ ID No: 3.

6. The composition of claim 4, wherein the recombinant protein consists of the C-terminal knob domain and the adjacent 34 amino acids of the shaft domain of the EDS fiber capsid protein, as denoted by SEQ ID NO: 4.

7. A method for vaccinating a domestic bird against a pathogenic adenoviral infection, wherein said pathogen is HEV (hemorrhagic enteritis virus) or EDS virus (Egg Drop Syndrome virus), said method comprising administering to the domestic bird an effective immunizing amount of the composition of claim 4.

8. The method of claim 7, wherein the recombinant protein consists of the C-terminal knob domain and the adjacent 48 amino acids of the shaft domain of the HEV fiber capsid protein, as denoted by SEQ ID NO: 3.

9. The method of claim 7, wherein the recombinant protein consists of the C-terminal knob domain and the adjacent 34 amino acids of the shaft domain of the EDS fiber capsid protein, as denoted by SEQ ID NO: 4.

10. The method of claim 7, wherein the composition is administered via injection, drinking water, feed, spraying, oral gavage and directly into the digestive tract of said domestic bird.

* * * * *